United States Patent [19]

Bezzegh et al.

[11] Patent Number: 4,680,315

[45] Date of Patent: Jul. 14, 1987

[54] POWDER MIXTURE HAVING HIGH PROPYLENE GLYCOL CONTENT AND PROCESS FOR THE PREPARATION THEREOF

[75] Inventors: Denes Bezzegh; Karoly Magyar; Jozsef Kelemen; Gabor Zalai; Attila Mandi; Janos Egri, all of Budapest, Hungary

[73] Assignee: EGYT Gyogyszervegyeszeti Gyar, Budapest, Hungary

[21] Appl. No.: 689,222

[22] Filed: Jan. 7, 1985

[30] Foreign Application Priority Data

Jan. 6, 1984 [HU] Hungary .................. 2251-39/84

[51] Int. Cl.$^4$ ........................................... A61K 31/045
[52] U.S. Cl. ..................... 514/738; 514/770; 514/23; 514/31
[58] Field of Search ............ 514/738, 769, 770; 424/23, 31, 156, 157

[56] References Cited

U.S. PATENT DOCUMENTS 3,235,451  2/1966  Odeneal ........................... 424/23

FOREIGN PATENT DOCUMENTS 57-72906  5/1982  Japan ............................... 514/770

Primary Examiner—Frederick E. Waddell
Attorney, Agent, or Firm—Keil & Weinkauf

[57] ABSTRACT

The invention refers to a powder mixture having a high propylene glycol content and a process for the preparation thereof. The powder mixture consists of 25 to 75 percent by weight of propylene glycol and 75 to 25 percent by weight of magnesium oxide and/or magnesium peroxide and/or magnesium carbonate as a solid carrier(s). The powder mixture can be treated as a solid powder and it does not deliquesce in the air even when stored for a long time. The mixture can be used as solid propylene glycol in dietetic products for calf, piglet and lamb, in pharmaceutical compositions for the treatment of ketosis and in other pharmaceutical compositions for veterinary use.

6 Claims, No Drawings

POWDER MIXTURE HAVING HIGH PROPYLENE GLYCOL CONTENT AND PROCESS FOR THE PREPARATION THEREOF

The invention relates to a powder mixture having high propylene glycol content and a process for the preparation thereof. The powder mixture of the invention can be employed for the preparation of veterinary compositions and animal feeds.

Propylene glycol can be extensively used in the field of veterinary medicine and animal husbandry. Thus, it is an important ingredient of the pharmaceutical compositions used in the treatment of ketosis in cattles. In addition, it can be employed to preserve feeds and improve the taste thereof, to hinder the formation of clouds of dust when mixing fine particles, and to avoid the segregation of particles in mixtures. Furthermore, propylene glycol is a fungicide and antioxidant in feeds and acts as a wetting agent in the dissolution of milk powder [Feed Additive Compendium, 1977, p. 300]. However, it is a serious problem that in most cases the liquid propylene glycol has to be homogenized with solid substances or mixtures, propylene glycol being often non-compatible with certain components thereof. A further difficulty is due to the very high hygroscopicity of propylene glycol since the solid mixtures comprising it can easily deliquesce on standing.

Since the difficulties listed above cannot be eliminated, the use of propylene glycol is limited. At present, propylene glycol is sprayed to the animal feeds directly before use, mostly at the place of use. However, it is required to have a homogenizing device equipped with a sprayer, to have available liquid propylene glycol e.g. in tank-trucks and to employ the animal feed comprising propylene glycol in a short time after preparation. Of course, every farm does not possess suitable devices to manufacture animal feeds comprising propylene glycol when needed. But it is not possible, either, to prepare huge quantities of animal feeds in factories and to transport the products to the farms since such mixtures cannot be stored for a longer time.

The aim of the invention is to eliminate the above difficulties and to provide a solid powder mixture comprising a high proportion of propylene glycol.

It has been found that the aims set can be reached by means of a powder mixture consisting of 25 to 75 percent by weight of propylene glycol and 75 to 25 percent by weight of a solid carrier selected from the group consisting magnesium oxide, magnesium peroxide, magnesium carbonate, silica and a mixture thereof. Surprisingly, the powder mixture of the invention comprising even 50 to 75 percent by weight of propylene glycol behaves as a solid, it can be easily admixed to other solid particles, it is not sticky and can be stored for a long time in a space having 75 percent of relative humidity without loosing its favourable properties.

It is also surprising for an expert that the carriers of the invention are able to bind even 75 percent by weight of propylene glycol without becoming deliquescent or at least sticky. Several organic and inorganic solid carriers have been examined and it has been found that e.g. calcium oxide, calcium carbonate, active carbon, bran or milk powder could bind 15 to 25 percent by weight of propylene glycol at the most, and the products obtained became deliquescent within some hours.

In the specification the term "powder mixture" is a product comprising one, two or more solid carriers and propylene glycol bound to the carrier(s). The product consisting of one solid carrier such as magnesium oxide and propylene glycol is also defined as powder mixture since the normally liquid propylene glycol present in the mixture of the invention behaves as a solid.

Thus, the powder mixture of high propylene glycol content of the invention consists of 25 to 75 percent by weight, preferably 40 to 55 percent by weight, of propylene glycol and 75 to 25 percent by weight, preferably 60 to 45 percent by weight of magnesium oxide and/or magnesium peroxide and/or magnesium carbonate and/or silica.

The preferred powder mixture of the invention comprises magnesium oxide and silica or magnesium carbonate or silica in a weight ratio of 4 to 1 as solid carriers. These carriers are especially suitable to bind 50 to 75 percent by weight of propylene glycol.

The powder mixture of the invention is prepared by admixing the components thereof. Preferably, propylene glycol is sprayed onto the carrier(s) until the required propylene glycol content is reached. It is also possible to spray the propylene glycol to only a part of the amount of carrier(s) and to admix the remaining amount of the carrier(s) to the mixture obtained.

The conventional homogenizing devices can be used for mixing the ingredients of the powder mixture of the invention. Preferred devices are blenders of eddy current and intensive blenders that can be equipped with spraying nozzles.

The powder mixture of the invention having even as much as 75 percent of propylene glycol content can be treated as a solid powder and can be admixed to other solid particles without difficulty. Although the hygroscopicity of the propylene glycol present in the powder mixture is unchanged, the mixture does not deliquesce even when it is stored for a long time in the air. The solid carriers present in the mixture neither disturb the conventional uses of propylene glycol nor have any unfavourable side-effects. From the point of view of use, the powder mixture of the invention can be treated as a solid propylene glycol.

The powder mixture of the invention can be employed as an ingredient in dietetic products for calf, piglet and lamb in addition to usual ingredients such as greases, proteins, vitamine and conventional additives; in pharmaceutical compositions for the treatment of ketosis in cattle, and in other pharmaceutical compositions for veterinary use.

The powder mixture of the invention can be manufactured extremely easily and it eliminates the difficulties experienced with liquid propylene glycol.

The invention is further elucidated by the aid of the following Examples.

EXAMPLE 1

40 parts by weight of powdered magnesium carbonate (80 percent of which are lower than 10 $\mu$m in particle size) are transferred into an eddy current blender of Lödige type equipped with spraying nozzles. Mixing is started and 50 parts by weight of propylene glycol are sprayed at a steady rate. Mixing is continued for further 15 minutes, then 10 parts by weight of finely divided silica (manufacturer: Degussa, West-Germany) are added and the mixture is homogenized for further 10 minutes. If desired, the mixture obtained is passed through a sieve having a mesh size of 1000 $\mu$m.

The mixture obtained contains 50 percent by weight of propylene glycol, 40 percent by weight of magnesium carbonate and 10 percent by weight of silica. It is perfectly dry and powdery. The particle size of 80 percent of the product is lower than 800 μm. The loose bulk volume equals to 4.4 cm$^3$/g. The packed bulk volume determined by means of Engelsmann volumeter (manufacturer: Engelsmann, West-Germany) using an impact number of 1500 is 3.3 cm$^3$/g. When the product is kept at 25° C. in a relative humidity of 75 percent for 30 days, the weight gains by 15 percent but the mixture remains powdery.

EXAMPLE 2

60 parts by weight of propylene glycol are sprayed to 40 parts by weight of powdered magnesium oxide (90 percent of which are lower than 10 μm in particle size) as described in Example 1. The product comprising 60 percent by weight of propylene glycol and 40 percent by weight of magnesium oxide is perfectly dry and powdery.

EXAMPLE 3

70 parts by weight of propylene glycol are sprayed to 30 parts by weight of magnesium carbonate as described in Example 1. The product obtained is powdery and consists of 70 percent by weight of propylene glycol and 30 percent by weight of magnesium carbonate.

EXAMPLE 4

Propylene glycol is sprayed to magnesium peroxide as described in Example 1. The powdery product obtained contains 52 percent by weight of propylene glycol.

EXAMPLE 5

Propylene glycol is sprayed to powdery silica (manufacturer: Degussa, West-Germany) as described in Example 1. The powdery product obtained consists of 25 percent by weight of silica and 75 percent by weight of propylene glycol.

EXAMPLE 6

50 parts by weight of propylene glycol are sprayed to 50 parts by weight of magnesium carbonate as described in Example 1. The powdery product obtained contains 50 percent by weight of propylene glycol and 50 percent by weight of magnesium carbonate.

EXAMPLE 7

The products prepared according to any of Examples 1 to 6 can be used for the preparation of a pharmaceutical composition for the treatment of ketosis. Thus, the usual ingredients of the compositions against ketosis in cattle such as methionine, calcium propionate, vitamines, mineral salts, dextrose etc. are homogenized with 8 to 12 percent by weight of the product prepared according to any of Examples 1 to 6. The powdery pharmaceutical composition obtained can be stored for a long time.

EXAMPLE 8

3 to 6 percent by weight of the product prepared according to any of Examples 1 to 6 are admixed with 15-17 percent by weight of a grease mixture, 70-78 percent by weight of animal feed containing protein and 1-3 percent by weight of additives consisting of vitamines and other substances having biological activity. The mixture obtained can be used as a dietetic product for calf. A dietetic product of similar composition can be prepared also for piglet. In such mixtures the additives may comprise amino acids and microelements, too.

EXAMPLE 9

3 to 6 percent by weight of the product prepared according to any of Examples 1 to 6 are admixed with 25-30 percent by weight of a grease mixture, 60-70 percent by weight of milk powder and 1-3 percent by weight of additives consisting of vitamines, amino acids, flavourants and other substances having biological activity. The mixture obtained can be used as a dietetic product for lamb.

EXAMPLE 10

To 60 parts by weight of alfalfa meal 26 parts by weight of wheat starch, 4 parts by weight of a product obtained according to Example 6 and 10 parts by weight of 2-formyl-quinoxaline-1,4-dioxide carbomethoxyhydrazone (carbadox) are admixed in the sequence given. The mixture obtained is a premix that can be diluted with the conventional feeds of pigs to promote the utilization of the feed by the animals. When mixing the components of the premix, the use of the powder mixture having high propylene glycol content eliminates the explosion hazard associated with the mechanical treatment of dry carbadox.

What we claim is:

1. A method of incorporating propylene glycol into veterinary medicines and animal feeds which comprises: mixing propylene glycol with a solid carrier selected from the group consisting of magnesium oxide, magnesium peroxide and magnesium carbonate and mixtures thereof in a weight ratio of from 75 to 25% propylene glycol to 25 to 75% of solid carrier to form a powder mixture, and thereafter incorporating the mixture into the veterinary medicine or animal feed.

2. The method of claim 1, wherein the mixture of propylene glycol and solid carrier contains from 40 to 55% by weight of propylene glycol.

3. The method of claim 1, wherein the solid carrier consists essentially of magnesium oxide.

4. The method of claim 1, wherein the solid carrier consists essentially of magnesium carbonate.

5. The method of claim 1, wherein the mixture of propylene glycol and solid carrier is added to a dietetic feed for calves, pigs or lambs.

6. The method of claim 1, wherein the mixture of propylene glycol and solid carrier is added to a pharmaceutical product for treating ketosis in cattle.

* * * * *